(12) United States Patent
Mayeski

(10) Patent No.: US 10,524,782 B2
(45) Date of Patent: Jan. 7, 2020

(54) LOW FRICTION FLAT BRAID

(71) Applicant: TELEFLEX MEDICAL INCORPORATED, Morrisville, NC (US)

(72) Inventor: Carsten Robert Mayeski, Sharon, MA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 212 days.

(21) Appl. No.: 15/334,125

(22) Filed: Oct. 25, 2016

(65) Prior Publication Data

US 2017/0112497 A1    Apr. 27, 2017

Related U.S. Application Data

(60) Provisional application No. 62/246,775, filed on Oct. 27, 2015.

(51) Int. Cl.
*A61B 17/06* (2006.01)
*A61B 17/00* (2006.01)

(52) U.S. Cl.
CPC ........... *A61B 17/06166* (2013.01); *A61B 2017/00526* (2013.01); *A61B 2017/00849* (2013.01); *A61B 2017/0618* (2013.01)

(58) Field of Classification Search
CPC ............. A61B 17/06166; A61B 2017/00526
USPC ............................. 606/228; 623/13.19, 13.2
See application file for complete search history.

(56) References Cited

U.S. PATENT DOCUMENTS

| | | | | |
|---|---|---|---|---|
| 3,357,171 A | * | 12/1967 | Marshall | D02G 3/34 57/207 |
| 3,565,077 A | * | 2/1971 | Glick | A61B 17/06166 606/231 |
| 4,792,336 A | * | 12/1988 | Hlavacek | A61F 2/06 623/13.18 |
| 6,716,234 B2 | * | 4/2004 | Grafton | A61B 17/06166 606/228 |
| 7,294,406 B2 | * | 11/2007 | Canham | A61B 17/06166 428/446 |
| 8,177,839 B2 | * | 5/2012 | Koob | A61L 27/24 623/13.11 |

(Continued)

FOREIGN PATENT DOCUMENTS

| | | |
|---|---|---|
| EP | 1543782 A1 | 6/2005 |
| EP | 1844797 A1 | 10/2007 |

(Continued)

OTHER PUBLICATIONS

Written Opinion of the International Searching Authority and International Search Report (ISR) (PCT Form PCT/ISA/210) dated Feb. 23, 2017, in International Patent Application No. PCT/US16/58596.

*Primary Examiner* — Julian W Woo
(74) *Attorney, Agent, or Firm* — Baker & Hostetler LLP

(57) ABSTRACT

A dry sliding low friction suture having an undulated surface is provided. The suture includes: a first end; and a second end braided with the first end to form the suture having an undulated surface having high portions and low portions, and wherein the first end and the second end are of different Denier thereby causing the first and second end to have different diameters which forms the high portion and low portions when all of the ends are braided together.

32 Claims, 2 Drawing Sheets

(56) References Cited

U.S. PATENT DOCUMENTS

| | | | |
|---|---|---|---|
| 8,414,612 B2 | 4/2013 | Kirsch et al. | |
| 8,641,732 B1 | 2/2014 | Goraltchouk et al. | |
| 8,715,317 B1 * | 5/2014 | Janardhan | A61F 2/01 606/200 |
| 8,881,635 B2 * | 11/2014 | Martin | A61B 17/06166 87/6 |
| 9,314,244 B2 * | 4/2016 | Spivey | A61B 17/06166 |
| 9,474,520 B2 * | 10/2016 | Olson | A61L 17/04 |
| 2009/0105753 A1 * | 4/2009 | Greenhalgh | A61L 17/145 606/228 |
| 2009/0112251 A1 * | 4/2009 | Qian | A61B 17/12022 606/194 |
| 2010/0298872 A1 | 11/2010 | Berndt et al. | |
| 2012/0197294 A1 | 8/2012 | Martin | |
| 2013/0317545 A1 | 11/2013 | Gross et al. | |
| 2014/0081295 A1 | 3/2014 | Lau et al. | |
| 2015/0173753 A1 | 6/2015 | Spivey et al. | |

FOREIGN PATENT DOCUMENTS

| | | |
|---|---|---|
| RO | 123135 B1 | 12/2010 |
| WO | 2010100488 A1 | 9/2010 |

\* cited by examiner

LOW FRICTION FLAT BRAID

This application is a Non-Provisional Applications and claims priority to provisional U.S. patent application entitled, Low Friction Flat Braid, filed Oct. 27, 2015, having a Ser. No. 62/246,775, the disclosure of which is hereby incorporated by reference in its entirety.

FIELD OF THE DISCLOSURE

The present disclosure relates generally to a flat braid suture. More particularly, the present disclosure relates to a low friction flat braid having an undulated surface.

BACKGROUND OF THE INVENTION

Sutures are used within the human body during surgical operations. Sometimes flat braided sutures are used and sometimes they may cause post-operative irritation when the suture is implanted in a place or manner where repetitive sliding occurs. Sutures having higher coefficients of friction may sometimes lead to higher loads on the anchor sites as well as irritation where the suture is sliding, particularly if the suture is sliding on bone or cartilage.

Lower friction surfaces may be sought after in sutures in order to reduce irritation. One approach is to find more lubricious materials to use in the suture. Sutures that slide on hard surfaces are subject to wear and the resulting wear debris causes plowing and causes an increased frictional force. This can sometimes cause an undesirable amount of irritation for the patient and higher loads on anchor sites of the suture.

Accordingly, it is desirable to provide a method and apparatus that provides a suture having a relatively low amount of sliding friction and therefore be less irritable to patients and reduced anchor sites of the suture.

SUMMARY OF THE DISCLOSURE

The foregoing needs are met, to a great extent, by the present disclosure, wherein in one aspect an apparatus is provided that in some embodiments a suture having a relatively low amount of sliding friction and therefore be less irritable to patients and/or reduced loads at anchor sites of the suture.

In accordance with one embodiment of the present invention, a dry sliding low friction suture having an undulated surface is provided. The suture includes: a first end; and a second end braided with the first end to form the suture having an undulated surface having high portions and low portions, and wherein the first end and the second end are of different Denier thereby causing the first and second end to have different diameters which forms the high portion and low portions when all of the ends are braided together.

In accordance with another embodiment of the present invention, a dry sliding low friction suture having an undulated surface is provided. The suture includes: a first end; and a second end braided with the first end to form the suture having an undulated surface having high portions and low portions wherein the first end and the second end were braided at different tensions form each other causing the undulated surface.

In accordance with another embodiment of the present invention, a method of forming a suture having an undulated surface is provided. The method includes: braiding a first end together with a second end to form a suture; forming with the braid an undulated surface having high and low portions in the suture; and braiding the first and second ends tightly so that the ends are firmly in place and there are no gaps when bending or twisting the suture by hand.

In accordance with yet another embodiment of the present invention, a suture having an undulated surface is provided. The suture includes: a first end; and a second end braided with the first end to form the suture having an undulated surface having high portions and low portions, wherein the first end and the second end are of different Denier thereby causing the first and second ends to have different diameters which forms the high portion and low portions when the first and second ends are braided together, and wherein a distance between two adjacent high portion is about 50-150 microns.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
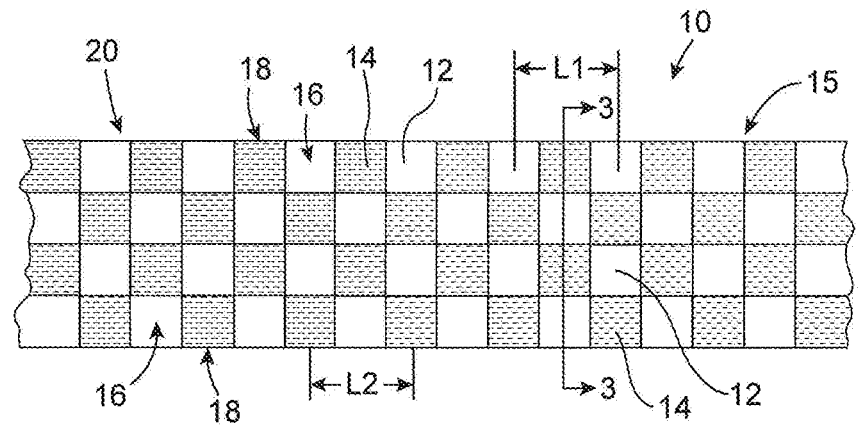
FIG. 1 is an enlarged, partial, top view illustrating a suture in accordance with an embodiment of the disclosure.

The various embodiments will now be described with reference to the drawing figures, in which like reference numerals refer to like parts throughout. An embodiment in accordance with the present disclosure provides a suture having and undulated surface. In some embodiments, the suture will be used in conditions where the suture may slide against a surface of greater or equal hardness as the suture, such as an implant, cartilage, or bone. In some embodiments, the way the suture is shaped and made may result in the design having a smaller coefficient of friction than a suture formed in a traditional manner regardless of the initial lubricity of materials used to form the suture in question.

An embodiment of the present inventive apparatus is illustrated in FIG. 1. FIG. 1 illustrates a partial top view of a suture 10. The suture 10 is made of two types of strands or ends 12 and 14 braided together to form a flat suture 10. The suture 10 includes a first end 12 and a second end 14.

In some embodiments, the ends 12 and 14 may be made of a variety of materials. For example, ultra-high-molecular-weight polyethylene (UHMWPE) may be used to make one or both of the ends 12 and 14. Alternatively one or both of the ends 12 and 14 may be made of polyester. The same suture 10 may include ends 12 and 14 of different materials such as, but not limited to UHMWPE and polyester. Using polyester in at least one of the ends 12 and 14 may give the suture 10 better knot security.

As shown in FIG. 1, the suture 10 has an undulated surface 15. The undulated surface 15 gives the suture 10 a lower coefficient of friction than a suture 10 of similar size and material with a flat surface in both dry and lubricated sliding conditions.

The undulated surface 15 has high portions 16 (shown by the lighter colored portions in FIG. 1) and low portions 18 (shown as the darker colored portions 18 in FIG. 1). The combination of the high portions 16 and the low portions 18 form a checkerboard pattern 20.

Figure 2:
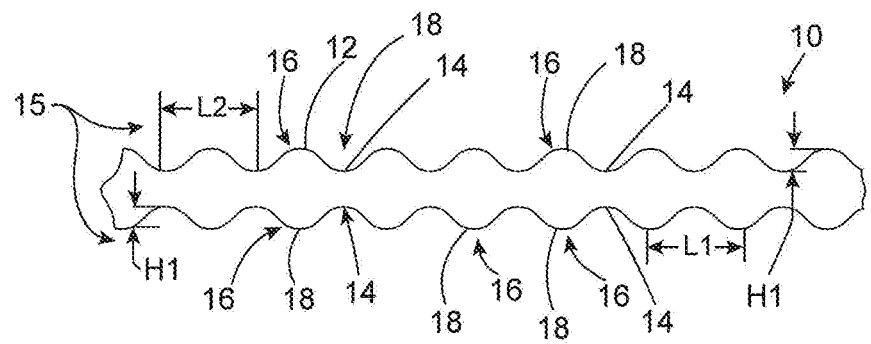
FIG. 2 is a partial side view of the suture of FIG. 1.

FIG. 2 is a side view of the portion of the suture 10 illustrated in FIG. 1. The undulated surface 15 of the suture 10 can clearly be seen. The first end 12 defines the high portions 16 and the second end 14 defines the low portions 18. The difference between the high portions 16 and the low portions 18 is illustrated by H1. In some embodiments, H1 is about 25-125 microns. Other differences in heights may also be used.

In FIGS. 1 and 2, L1 is shown to be the length between the high portions 16 and L2 is shown to be the length between the low portions 18. In some embodiments L1 is equal to L2. In other embodiments L1 and L2 are not equal. It is desirable to select the length of L1 and L2 so that they are not so long as to permit wear debris to move along with the suture 10 and cause plowing and increased friction. Keeping L1 and L2 (particularly L1) short, aids in reducing the likelihood of wear debris from being carried in the low portions 18 of the suture 10 and causing friction. In some embodiments, L1 and L2 are each in the range of 50-150 microns.

Figure 3:
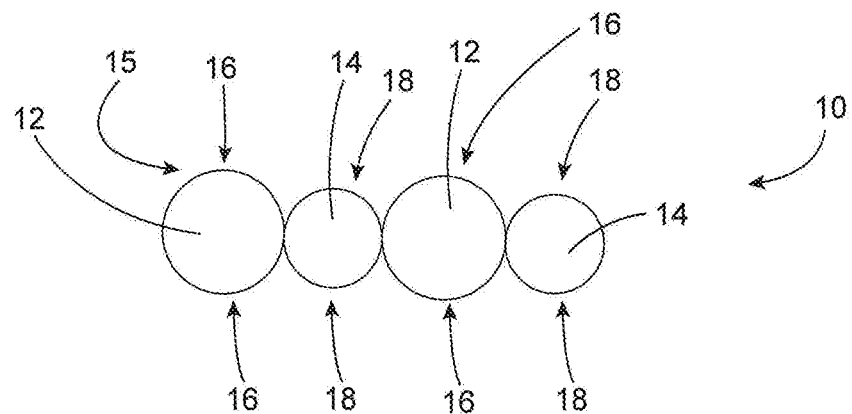
FIG. 3 is a cross-sectional view taken along the 3-3 in FIG. 1.

In FIG. 3 is a cross-section of the suture 10 illustrated in FIG. 1. The first group of ends 12 is shown to have a greater diameter than the second group of ends 14. The high portions 16 corresponds with the first end 12 and the low portion 18 corresponds with the second end 14. It is the difference in the diameters between the first ends 12 and the second end 14 which creates the undulated surface 15 which, as shown in FIG. 1, is in a checkerboard pattern 20.

In some embodiments, the Deniers of the two ends 12 and 14 are different which results in the two ends 12 and 14 having different diameters. In some embodiments, the first end 12 may have a Denier of 100 and the second end 14 may have a Denier of 55. In other embodiments, end 12 may be sized at 215 Denier and end 14 may be sized at 100 Denier. In other embodiments, the ends 12 and 14 may sized to have other Deniers. In some embodiments, the difference of the two sets of ends 12 and 14 may be 40 to 115 Denier.

Figure 4:
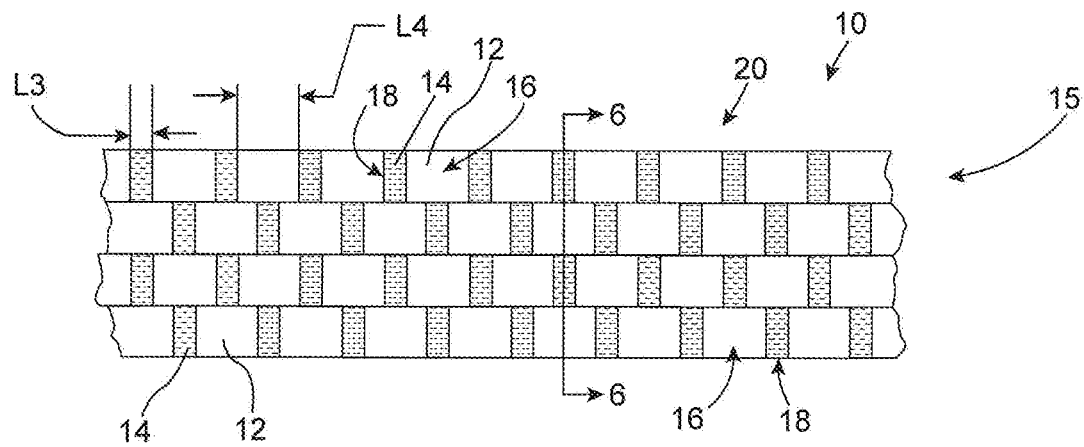
FIG. 4 is an enlarged, partial, top view illustrating a suture in accordance with another embodiment of the disclosure.
Figure 5:
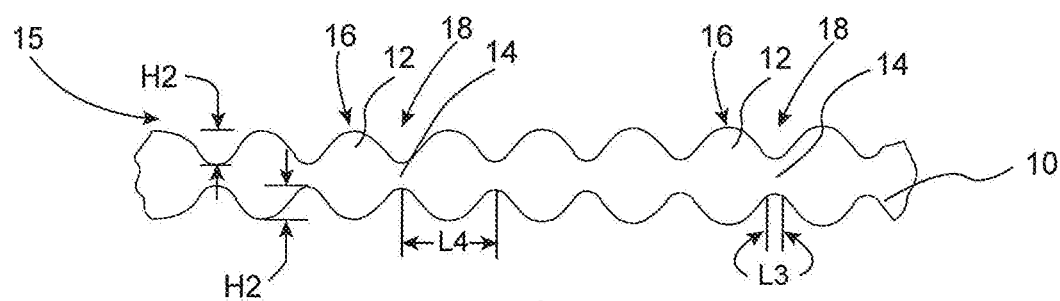
FIG. 5 is a partial side view of the suture of FIG. 4.
Figure 6:
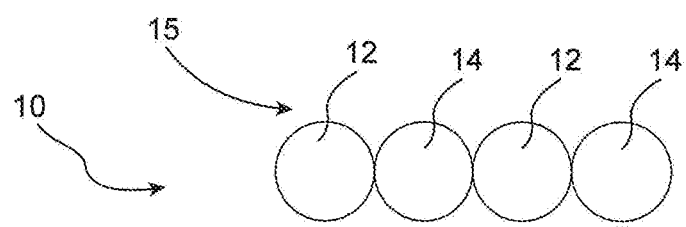
FIG. 6 is a is a cross-sectional view taken along the 6-6 in FIG. 4.

FIGS. 4, 5, and 6 illustrate a second embodiment having similar views as those shown in FIGS. 1-3. FIG. 4 illustrates a partial enlarged top view of a suture 10 having a first end 12 and second end 14. The suture 10 has an undulated surface 15 comprised of high portions 16 and low portions 18 which are represented by light and dark surfaces respectively. The light and dark surfaces representing the high portion 16 low portion 18 are set out in a checkerboard pattern 20 that is slightly different than that shown in the embodiment of FIG. 1.

As can be seen in FIG. 4, the low portions 18 are smaller in size compared to the high portions 16. For example, L3 as shown in FIG. 4 represents the length of the low portion 18. L4 represents the length of the high portion 16. As shown in FIG. 4, L4 is longer than L3. In other embodiments, L4 may be longer than L4 or, alternatively, L3 and L4 may be similar in length. As a result, the embodiment shown in FIG. 4 is checkerboard like, but the "squares" of the checkboard are rectangular not square. For the reasons set forth above with respect to L1 and L2 in FIGS. 1 and 2, it is desired to keep the length of L3 and L4 from being too long. In some embodiments L3 is in the range of 25-75 microns and L4 is in the range of 50-150 microns.

FIG. 5 is a partial side view of the suture 10 shown in FIG. 4. As can be seen in FIG. 5, the first end 12 corresponds with the high portion 16 and the second end 14 corresponds with the low portion 18. The high 16 and low portions 18 together form the undulated surface 15. The difference between the high portions 16 and the low portions 18 is illustrated by H2. In some embodiments, H2 is about 25-125 microns. In other embodiments, other differences in heights may also be used.

FIG. 6 is a cross-sectional view of the suture 10 taken along the line 6-6 in FIG. 4. The first end 12 and second end 14 are shown lined up next to each other. As can be seen in FIG. 6 the first end 12 and the second end 14 are roughly the same diameter. In such an embodiment, the first end 12 and the second end 14 may have the same Denier.

The ends 12 and 14 may be made of a variety of materials. For example, ultra-high-molecular-weight polyethylene (UHMWPE) may be used to make one or both of the ends 12 and 14. Alternatively one or both of the ends 12 and 14 may be made of polyester. The same suture 10 may include ends 12 and 14 of different materials such as, but not limited to UHMWPE and polyester. Using polyester in at least one of the ends 12 and 14 may give the suture 10 better knot security.

The undulated surface 15 illustrated in FIG. 4 is created where the two ends 12 and 14 are the same size fibers but the tightness of the braid has been altered. In some embodiments the two ends 12 and 14 may not exceed about 100 microns in diameter.

In some embodiments, the checkerboard like pattern 15 shown in FIG. 4 having high portions 16 and low portions 18 may be achieved by braiding ends 12 and 14 of same or similar diameter or Denier at a low braid angle with respect to the braiding machine bobbin. For example the braid may be formed tight enough so that the ends 12 and 14 are firmly in place and those are no gaps when handling bending or twisting the suture 10 by hand. Alternatively, the high portions 16 and low portions 18 forming the checkerboard like pattern 15 of FIG. 4 may be achieved by having the all ends braided under different tensions.

While the illustrated figures only show two ends 12 and 14 and show the suture to only be four ends 12 and 14 wide, it should be understood that this has been simplified to better explain the various embodiments. It will be appreciated that some embodiments will use more or fewer ends 12 and 14 in the suture 10. Many sutures 10 will incorporate many more ends 12 and 14 than four in the braid of the suture 10. It may be appreciated that end 12 may represent all of the ends having the Denier or diameter of end 12 and end 14 may represent all of the ends having the Denier or diameter of end 14.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A dry sliding low friction suture having an undulated surface, the suture comprising:
   at least one first strand having a first Denier and a first diameter; and
   at least one second strand braided with the at least one first strand, the at least one second strand having a second Denier and a second diameter,
   wherein the first Denier is greater than the second Denier, the first diameter is greater than the second diameter, the at least one first strand forms high portions of the undulated surface, the at least one second strand forms low portions of the undulated surface, and the first and second strands are braided tightly such that no gaps are formed therebetween.

2. The suture of claim 1, wherein the suture is a flat braid.

3. The suture of claim 1, wherein at least one of the first and second strands is made of ultra-high-molecular-weight polyethylene (UHMWPE).

4. The suture of claim 1, wherein at least one of the first and second strands is made of polyester.

5. The suture of claim 1, wherein the first and second strands are made of the same material.

6. The suture of claim 1, wherein the first and second strands are made of different materials.

7. The suture of claim 1, wherein the first Denier is about 100-215.

8. The suture of claim 1, wherein the second Denier is about 55-100.

9. The suture of claim 1, wherein a distance between adjacent high portions of the undulated surface is between about 50-150 microns.

10. The suture of claim 9, wherein the first and second strands are no greater than 100 microns in diameter.

11. The suture of claim 1, wherein the undulated surface extends along a length and a width of the suture in a checkerboard pattern.

12. The suture of claim 1, wherein the at least one first strand comprises a plurality of first strands, and the at least one second strand comprises a plurality of second strands.

13. A dry sliding low friction suture having an undulated surface, the suture comprising:
   at least one first strand having a first diameter; and
   at least one second strand braided with the at least one first strand and having a second diameter,
   wherein the first diameter is greater than the second diameter, the at least one first strand forms high portions of the undulated surface, the at least one second strand forms low portions of the undulated surface each of, the high portions and low portions forms a substantially rectangular or square shape such that a generally checkerboard pattern is formed on the undulated surface, and the first and second strands are braided tightly such that no gaps are formed therebetween.

14. The suture of claim 13, wherein the difference in diameter between the first and second strands is about 40-115 Denier.

15. The suture of claim 13, wherein a difference in height between high and low portions of the undulated surface is about 10-15 microns.

16. The suture of claim 13, wherein the undulated surface extends along a length of the suture.

17. The suture of claim 13, wherein the undulated surface extends along a width of the suture.

18. The suture of claim 13, wherein the suture has a cross-section where the first and second strands are lined up next to each other.

19. The suture of claim 13, wherein the suture is a flat braid.

20. The suture of claim 14, wherein at least one of the first and second strands is made of ultra-high-molecular-weight polyethylene (UHMWPE).

21. The suture of claim 14, wherein at least one of the first and second strands is made of polyester.

22. The suture of claim 14, wherein the first and second strands are made of the same material.

23. The suture of claim 14, wherein the first and second strands are made of different materials.

24. The suture of claim 14, wherein a distance between adjacent high portions of the undulated surface is between about 50-150 microns.

25. The suture of claim 14, wherein the first and second strands are no greater than 100 microns in diameter.

26. The suture of claim 14, wherein the at least one first strand comprises a plurality of first strands, and the at least one second strand comprises a plurality of second strands.

27. A method of forming a suture having an undulated surface, the method comprising:
   braiding at least one first strand with at least one second strand, the at least one first strand having a first diameter and a first Denier, the at least one second strand having a second diameter and a second Denier, the first diameter being greater than the second diameter, and the first Denier being greater than the second Denier; and
   forming high portions of the undulated surface with the at least one first strand and low portions of the undulated surface with the at least one second strand,
   wherein the first and second strands are braided tightly such that no gaps are formed therebetween when bending or twisting the suture by hand.

28. The method of claim 27, wherein the at least one first strand is made of ultra-high-molecular-weight polyethylene (UHMWPE).

29. The method of claim 27, wherein the at least one second strand is made of polyester.

30. The suture of claim 27, wherein the at least one first strand comprises a plurality of first strands, and the at least one second strand comprises a plurality of second strands.

31. A suture having an undulated surface, the suture comprising:
   at least one first strand having a first Denier and a first diameter; and
   at least one second strand braided with the at least one first strand, the at least one second strand having a second Denier,
   wherein the first Denier is greater than the second Denier, the first and second strands have different diameters, the at least one first strand forms high portions of the undulated surface, the at least one second strand forms low portions of the undulated surface, a distance between adjacent high portions is about 50-150 microns, and the first and second strands are braided tightly such that no gaps are formed therebetween.

32. The suture of claim 17, wherein the at least one first strand comprises a plurality of first strands, and the at least one second strand comprises a plurality of second strands.

\* \* \* \* \*